(12) United States Patent
Henry

(10) Patent No.: US 9,504,487 B2
(45) Date of Patent: Nov. 29, 2016

(54) UNIVERSAL SCALPEL BLADE REMOVER

(71) Applicant: Qlicksmart Pty Ltd, Brisbane, Queensland (AU)

(72) Inventor: Robert Anthony Neville Henry, Brisbane (AU)

(73) Assignee: QLICKSMART PTY LTD, Brisbane, Queensland (AU)

(*) Notice: Subject to any disclaimer, the term of this patent is extended or adjusted under 35 U.S.C. 154(b) by 114 days.

(21) Appl. No.: 14/385,982

(22) PCT Filed: Mar. 25, 2013

(86) PCT No.: PCT/AU2013/000294
§ 371 (c)(1),
(2) Date: Sep. 17, 2014

(87) PCT Pub. No.: WO2013/142897
PCT Pub. Date: Oct. 3, 2013

(65) Prior Publication Data
US 2015/0047170 A1 Feb. 19, 2015

(30) Foreign Application Priority Data

Mar. 26, 2012 (AU) ................................ 2012901221

(51) Int. Cl.
*A61B 17/3217* (2006.01)
(52) U.S. Cl.
CPC .... *A61B 17/3217* (2013.01); *A61B 2090/0803* (2016.02); *Y10T 29/49822* (2015.01); *Y10T 29/53596* (2015.01); *Y10T 29/53657* (2015.01); *Y10T 29/53991* (2015.01)
(58) Field of Classification Search
CPC .................... A61B 17/3217; Y10T 29/53596; Y10T 29/53657; Y10T 29/49822; Y10T 29/53991
See application file for complete search history.

(56) References Cited

U.S. PATENT DOCUMENTS

| 4,730,376 A | 3/1988 | Yamada | |
|---|---|---|---|
| 4,903,390 A * | 2/1990 | Vidal | A61B 17/3217 206/355 |
| 5,449,068 A * | 9/1995 | Gharibian | A61B 17/3217 206/355 |

FOREIGN PATENT DOCUMENTS

| EP | 0 005 052 A1 | 10/1979 |
|---|---|---|
| EP | 0 563 299 A1 | 11/1993 |

(Continued)

OTHER PUBLICATIONS

International Search Report (PCT/AU2013/000294)—Date of Mailing: May 28, 2013.

(Continued)

*Primary Examiner* — John C Hong
(74) *Attorney, Agent, or Firm* — Howard & Howard Attorneys PLLC

(57) ABSTRACT

A scalpel blade remover comprises a housing, and a planar member mounted in the housing with a longitudinal slot therein. A slider is adapted to slide along the planar member, and has an opening for receiving a portion of a tang therein. The slider is movable along the planar member when pressed by the tang being inserted into the opening and moved along the slot, with the blade being located under the slider. Movement of the slider along the planar member causes the planar member to separate the rear end of the blade from the tang. A stop formation on the planar member engages the rear end of the blade after it has been separated from the tang and prevents the blade being withdrawn along the member. Upon withdrawal of the tang, the blade is stripped from the tang.

20 Claims, 6 Drawing Sheets

(56) References Cited

FOREIGN PATENT DOCUMENTS

| WO | 83/00454 A1 | 2/1983 |
| WO | 91/03984 A1 | 4/1991 |
| WO | 96/07363 A1 | 3/1996 |
| WO | 97/26834 A1 | 7/1997 |

OTHER PUBLICATIONS

Written Opinion of the International Searching Authority (PCT/AU2013/000294)—Date of Mailing: May 28, 2013.

* cited by examiner

UNIVERSAL SCALPEL BLADE REMOVER

CROSS REFERENCE TO RELATED APPLICATION

This application is a national stage application of PCT/AU2013/000294, filed Mar. 25, 2013, which claims priority to Australian Patent Application No. 2012901221, filed Mar. 26, 2012, the disclosures of which are hereby incorporated by reference in their entirety.

TECHNICAL FIELD

This invention relates to a scalpel blade remover. In particular, the invention is directed to a scalpel blade remover suitable for removing blades of different sizes from tangs of different sizes.

BACKGROUND ART

International patent application no. PCT/AU95/00585, and its counterpart U.S. Pat. No. 5,875,533, disclose a scalpel blade remover for removing a blade from the tang of a scalpel. In use, the scalpel is inserted in, and withdrawn from, the blade remover along the same substantially straight-line path. The blade remover has a rocker block which pivots about an axis transverse to the insertion path. When the scalpel is inserted into the blade remover, the blade pushes against a distal contact surface of the rocker block, causing the rocker block to pivot. A pair of legs at the other (proximal) end of the rocker block apply a transverse force to the heel of the blade on either side of the tang, thereby lifting the heel of the blade off the tang. When the scalpel has been inserted far enough, a pawl or detent drops behind the heel of the blade. When the scalpel handle is withdrawn, the pawl or detent prevents the blade from being withdrawn, causing it to be stripped from the tang.

Although the scalpel blade remover of PCT/AU95/00585 and U.S. Pat. No. 5,875,533 operates well, and provides a safe and secure method for removing a blade from a scalpel, it is primarily suitable for use with scalpel blades and scalpel handles or tangs within a limited range of sizes and shapes.

However, scalpel blades and scalpel handles come in various shapes and sizes. It is therefore a preferred aim of the present invention to provide a scalpel blade remover which is suitable for removing a wide range of different sized blades from a wide range of different sized scalpel handles or tangs.

SUMMARY OF THE INVENTION

In one broad form, the invention provides a scalpel blade remover for removing a blade from a tang of a scalpel, the blade having a front end and a rear end, the scalpel blade remover comprising: a housing, a generally planar member mounted in the housing, the planar member having a longitudinal slot therein between spaced portions of the planar member, a slider member operatively associated with the planar member and adapted to slide along the planar member, the slider member having an opening for receiving at least a portion of the tang therein, the slider member being movable along the planar member when pressed by the tang of a user-held scalpel being inserted into the opening and moved along the slot in the planar member, wherein movement of the slider member along the planar member causes the spaced portions of the planar member to separate the rear end of the blade from the tang, and at least one stop formation mechanism on the planar member which, in use, engages the rear end of the blade after it has been separated from the tang and prevents the blade being withdrawn along the member, such that upon withdrawal of the scalpel, the blade is stripped from the tang thereof.

In a first embodiment, the planar member is pivotally mounted, and the scalpel blade remover includes a tilting mechanism actuated by movement of the slider member along the planar member to cause the planar member to pivot or tilt, and such pivoting or tilting action causes the spaced portions of the planar member to separate the rear end of the blade from the tang.

Preferably, the tilting mechanism is a cam operated mechanism, comprising a cam rod extending from the slider member and having a predetermined curved or angled profile. The forward or distal portion of the cam rod is constrained to pass through a fixed opening or over a fixed surface or edge. As the slider member is pushed along the planar member, the distal portion of the profiled cam rod passes through the fixed opening or over the fixed surface or edge to cause the slider member, and hence the planar member on which it is slides, to tilt about its pivot axis. As a result of this tilting action, the spaced portions of the planar member are urged against the rear end or heel of the blade on opposite sides of the tang, and separate it from the tang. (As the rear edge of the blade may be oblique, at least one of the spaced portions of the planar member is urged against the rear end or heel of the blade to separate it from the tang.)

Suitable means are provided to maintain the slider member in a close sliding relationship with the planar member. Preferably, the planar member has a tubular portion within which the slider slides for at least part of its travel. The tubular portion has a cross sectional shape which is dimensioned and configured to maintain the slider member in a close sliding relationship with the planar member as it moves through the tubular portion.

In a second embodiment, the planar member is fixedly mounted, preferably at an oblique angle to the direction of movement of the scalpel. The planar member is typically angled slightly downwardly towards the scalpel and relative to the plane of the insertion path of the scalpel. Due to this angled interaction of the planar member with the tang of the scalpel, the spaced portions of the planar member are urged against the rear end or heel of blade on opposite sides of the tang in a wedge action, and separate it from the tang.

The rod extending from the slider may be retained in this second embodiment, but it can be a straight rod.

Preferably, the slider member is resiliently biased to a rest position by biasing means. In a preferred embodiment, the biasing means comprises a coil spring located around the cam rod.

Preferably, the planar member is made of resiliently flexible material, enabling the longitudinal slot therein to expand to accommodate tangs of different sizes.

Preferably, the housing includes a shoulder or ledge, hereafter referred to as a landing pad, upon which the tang-mounted blade is placed at the start of the blade removal process. The ledge may have a shallow slot or channel therein. When the slider block is at its rest position, the slot of the slider block is located over the slot of the landing pad. The composite slots form the entry opening for the tang of scalpel blade remover, with the tang mounted blade being inserted between the slider block and the landing pad.

Preferably, the bottom surface of the slider block is tapered to form a slit-like entry opening with varying height, thereby accommodating blades of different thickness or widths.

Advantageously, two longitudinally spaced stop formations are provided on the tubular portion to provide more reliable stripping of blades of different sizes.

In the preferred embodiment, the housing includes a sharps container into which the blade drops after being stripped from the tang.

The scalpel blade remover may include a counter mechanism actuated by movement of the cam rod, to count the number of blades removed and stored in the sharps container. The counter mechanism may be configured to disable operation of the scalpel blade remover when the counter mechanism reaches a predetermined count.

In another form, the invention provides a method of removing a scalpel blade from the tang of a scalpel, comprising the steps of: providing a generally planar member having a longitudinal slot therein between spaced portions of the planar member, and a slider member adapted to slide along the planar member; inserting the tang into an opening in the slider member and into the slot, with the blade being located below the slider member; pushing the tang against the slider member to cause it to slide along the planar member, with the tang moving within the longitudinal slot, until the planar member engages the trailing end of the blade and prevents the blade being withdrawn along the member; and withdrawing the tang so that the blade is stripped from the tang.

In order that the invention may be more readily understood and put into practice, one or more preferred embodiments thereof will now be described, by way of example only, with reference to the accompanying drawings.

DETAILED DESCRIPTION OF PREFERRED EMBODIMENT(S)

Figure 1:
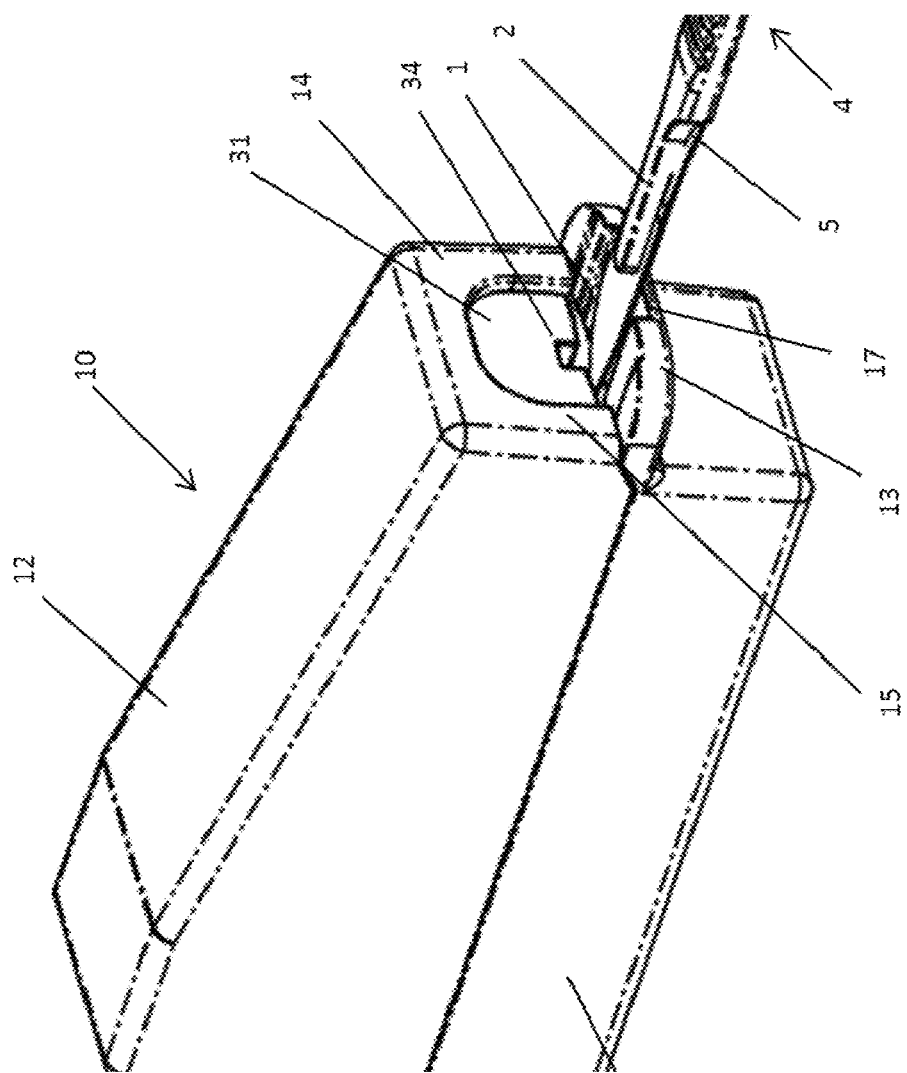
FIG. 1 is the perspective view of a scalpel blade remover according to a first embodiment of the invention.

For the purposes of this description, the illustrated embodiments of the scalpel blade remover are orientated in the drawings so that the top of the scalpel blade remover is towards the upper part of the page, and its front is towards the right hand side of the page, and terms used in the following description will be based on that orientation. However, it will be apparent to those skilled in the art that the scalpel blade remover may be used in any other orientation, including an upright or angled orientation.

As shown in FIG. 1, a first embodiment of a scalpel blade remover comprises an open-topped sharps container 10 having a lid or cover 12 mounted thereon. Both the container 11 and cover 12 may be made of suitable plastics material, and the cover 12 may be fixed to the container 11 at the manufacturing stage, e.g. by heat sealing, adhesive, screw fasteners or other suitable means. The container 11 may include a transparent portion [not shown] so that the quantity of its contents may be ascertained. The container 11 may also have a clamp mechanism [not shown] on its underside or end to permit the container to be mounted securely to a trolley, shelf, tray, table top or similar surface.

The cover 12 has an opening 15 on its front face 14.

Figure 3:
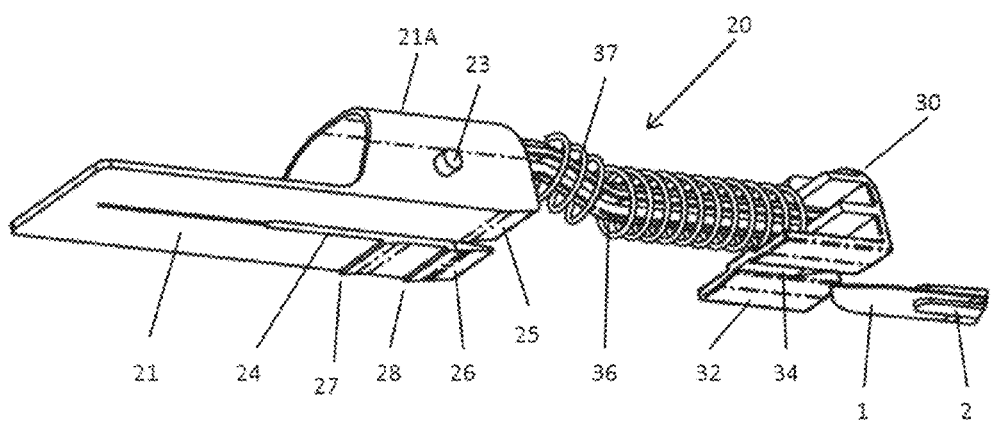
Figure 4:
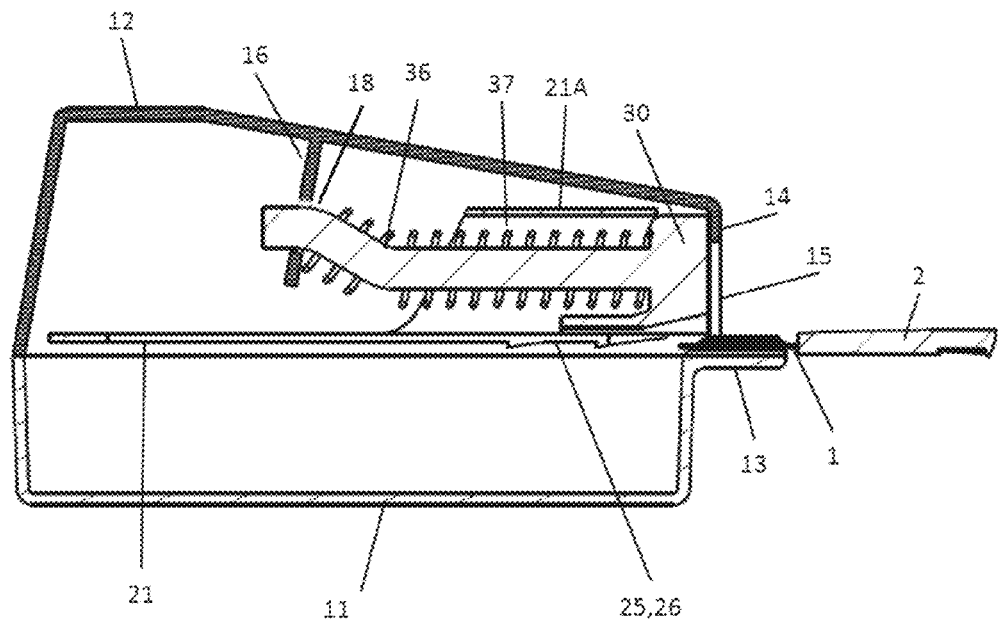
FIGS. 4 to 7 are sectional views of the scalpel blade remover of FIG. 1, illustrating progressive steps in the blade removal process.
Figure 5:
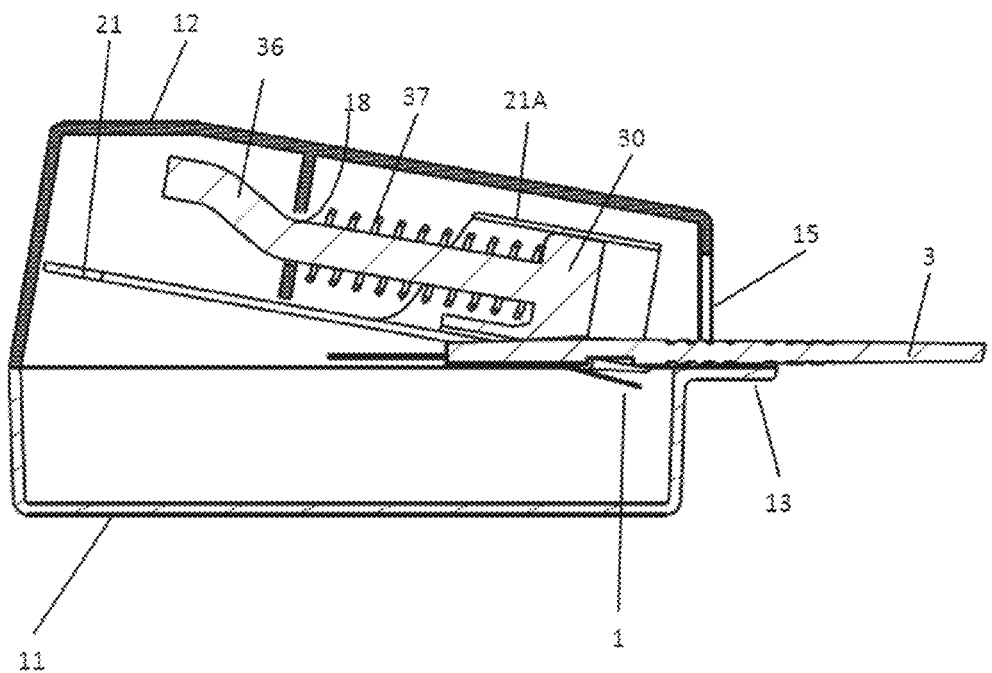

A blade removing mechanism 20 is mounted inside the cover 12 between its front face 14 and an internal flange 16, as shown in FIG. 4. The blade removing mechanism 20 is shown in more detail in FIGS. 2 and 3.

The blade removing mechanism 20 is designed to remove a blade 1 from the tang 2 at the forward end of the handle 3 of a scalpel 4. The tang 2 widens at its proximal end or base 5 to form the handle 3. The blade 1 has a slotted aperture, and a peripheral groove at the leading portion of the tang 2 receives portions of the edge of the aperture slot in the blade 1. The construction of the scalpel 3, and the mounting of the blade 1, are known in the art and need not be described in detail in this application.

The container 11 is provided with a flange which forms a ledge, which will be referred to as a 'landing pad' 13 in this description. The landing pad 13 is provided with a shallow channel or slot 17.

The blade removing mechanism 20 comprises a generally planar member 21 which has a flat upper surface which acts as a runway or platform as described in more detail below. The planar member 21 has a tubular portion 21A which defines a substantially straight tunnel portion 22. The tubular portion 21A of the planar member 21 is provided with a pair of pivot pins 23 on opposite sides thereof. These pivot pins locate in corresponding recesses [not shown] on the inside of the walls of the cover 12 in a form of trunnion mount, so that the planar member 21 may pivot about a pivot axis defined by the pivot pins 23. The pivot axis is transverse to the tunnel portion 22.

Figure 2:
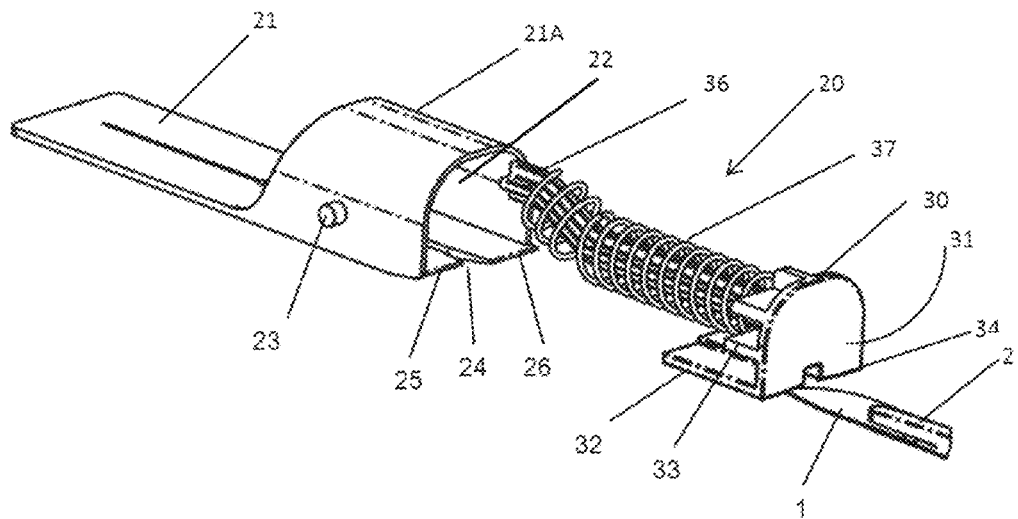
FIGS. 2 and 3 are the perspective views of the slider and stripper mechanism of the scalpel blade remover of FIG. 1.

A longitudinal slot 24 is provided in planar member 21. [Due to the presence of the slot 24, the tubular portion 21A is not continuous around the periphery of its section. Nevertheless, for the purposes of this specification, the portion 21A will be described as a tubular portion, and such references to 'tubular' are intended to include a generally tubular configuration as shown in FIGS. 2 and 3].

The planar member 21 and its tubular portion 21A are typically formed integrally from stiff but resiliently flexible plastics material. The longitudinal slot 24 divides the planar member 21 into two spaced portions 25, 26. Due to the flex in the material, the slot 24 may expand and contract, as described in more detail later. The front edges of the two spaced portions 25, 26 may optionally curve downwardly to a small extent (not shown).

Two longitudinally spaced stop members 27, 28 are integrally formed on the bottom of portion 26. These stop members 27, 28 are formed by transverse ridges on the underside of portion 26, having a sawtooth configuration, so that the stop members function as pawls or detents. The function of the stop members will be described in more detail later.

The blade removing mechanism also comprises a slider block 30 having a flat end and face 31 [which, in use, is located at the front of the scalpel blade remover and will also be referred to as the front face]. The slider block 30, also referred to herein simply as a 'slider' has a bottom portion 32 extending rearwardly and orthogonally to the front face 31, as well as a series of flanges 33 extending rearwardly and orthogonally from the front face 31. The bottom portion 32 may have a flat surface but preferably has ribs or flanges to provide a two point contact with the planar member and thereby reduce friction and manufacturing tolerances. The front face 31, bottom 32 and flanges 33 are configured and dimensioned so that the slider block 30 fits into the tunnel portion 22 in a close fit, but with sufficient tolerance to enable the slide block 30 to move freely along the tunnel portion 22. Moreover, the bottom 32 and flanges 33 are configured and dimensioned so that the slider block 30 is restrained to move in the tunnel portion 22 by translation only, i.e. the end face 31 does not rotate or tilt and maintains an orientation generally transverse to the longitudinal access of the tunnel. The slider 30 is also provided with a longitudinally extending opening, groove or slot 34 in the underside of its bottom portion 32, the slot having a front opening in the end face 31 of the slider 30.

The slider block 30 also has a cam rod 36 extending rearwardly therefrom. The cam rod 36 has a predetermined profile, i.e. the cam rod 36 has a predetermined curved or angled configuration.

When the scalpel blade remover 10 is assembled, the blade removing mechanism is located in the cover 10, so that the pivot pins 23 of the tubular portion 21A locate in corresponding recesses on internal sides of the cover 12 as previously stated, and the cam rod 36 extends through the tubular portion 21A and into an aperture 18 in the internal flange 16 of the cover 12. (The internal flange 16 may alternatively be made integral with the container 11 rather than the cover 12.) A coil spring 37 is provided around the cam rod 36, between the flange 16 and the slider 30, to bias the front face 31 of the slider against the inside of the end face 14 of the cover 12, thereby substantially closing the opening 15 in the end face 14 of the cover 12. At this location, the front face 31 of the slider 12 rests on the landing pad 13, and the slot 34 overlies the slot 17. The combination of the slots 34 and 17 form a composite opening for the tang 32 of the scalpel.

The space between the front face 31 and the landing pad 13 forms a narrow slit for accommodating the blade 21A mounted on the tang 2. Preferably, the bottom edges of the front face 31 are angled slightly, so that the blade slit has a thicker or wider opening in the middle, to accommodate blades of greater thickness or width.

The operation of the blade removable mechanism will now be described, with particular reference to FIGS. 4 to 7.

A scalpel having a blade to be removed is inserted into the scalpel blade remover 10 by first resting the tang 12 in the shallow slot 17 on the landing pad 12, and sliding the blade 1 between the slider 30 and the landing pad 13, and under the spaced portions 25, 26 [FIG. 4]. The block 30 can rise up slightly to accommodate thicker blades.

The scalpel is pushed forward so that the upper part of the tang enters the slot 34. The width of the tang 2 increases at its base, and hence when the tang is inserted far enough that the width of the tang 2 is as wide as the slot 34, the tang will engage the front face 31 of the slider 30, and push the slider into the cover 12. The relatively large opening 15 in the front face of the cover 12 accommodates even the largest scalpels used in practice.

As the slider 30 is pushed back into the tubular portion 21A by the tang 2 against the bias of the spring 37, the slider 30 slides along the runway-like portion of the planar member 21, and the bottom portion of the tang 2 travels along the longitudinal slot 24 in the planar member 21. Due to the resiliently flexible nature of the planar member 21, the slot 24 can expand to accommodate larger tangs.

When the slider 30 is initially pushed back into the cover 12, it makes contact with the planar member 21 and starts to tilt it about its pivot axis, and the profiled cam rod 36 engages with the bottom edge of the opening 18 through which it passes. Due to the cam-like interaction between the profiled rod 36 and the edge of the aperture 18, the slider block is urged further downwardly. As the slider block has been pushed back into the tubular portion 21A, the cam-like action positively causes the planar member 21 to pivot about the pivot pins 23 [FIG. 5]. The pivoting of the planar member 21, in turn, causes the spaced portions 25, 26 to put downward pressure on the rear end or heel of the blade 1 on opposite sides of the tang 2, thereby separating the heel of the blade from the tang. The resilient nature of the blade 1 keeps it pressed against the underside of the portions 25, 26.

Figure 6:
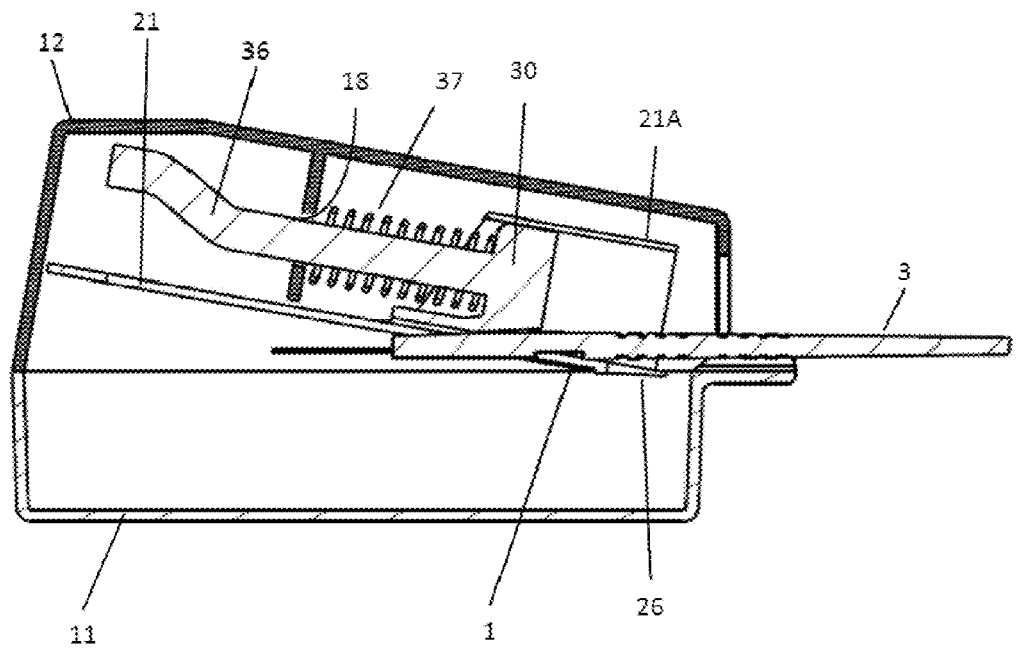
Figure 7:
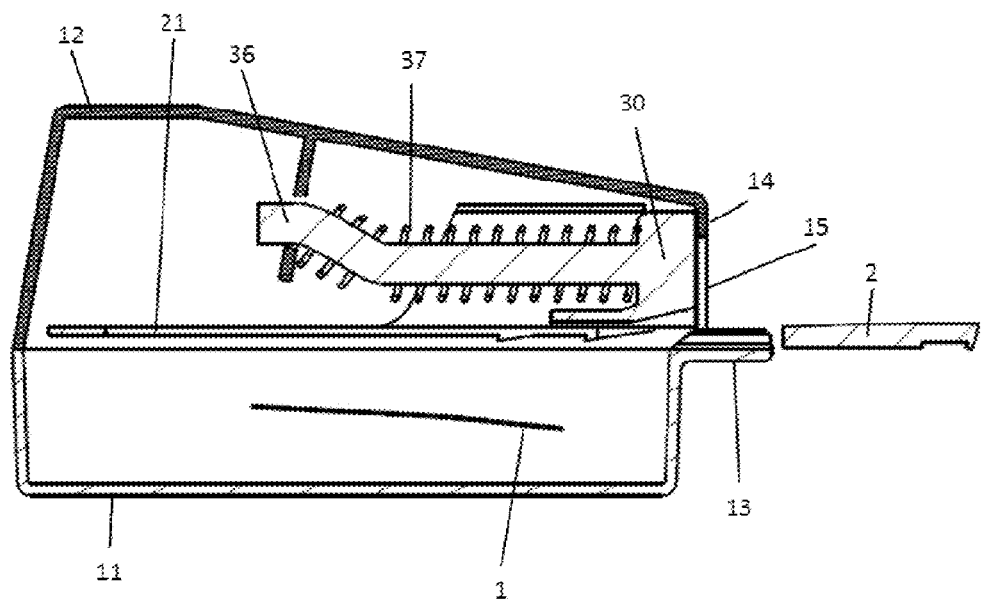

As the scalpel handle is pushed further into the opening 15, the proximal or heel end of the blade 1 will pass over the saw tooth ridge which forms the stop member 28 and snap back against the underside of the portion 26, generating an audible 'click' which indicates to the user that the scalpel has been inserted far enough and may now be withdrawn [FIG. 6]. Smaller blades may be inserted even further to engage against the distal stop member 27. Such blades can be captured with greater certainty since there are two stop members 27, 28 with which they may engage.

The scalpel is then withdrawn. As the stop member 28 (or 27) prevents the blade from being withdrawn, it is stripped from the tang 2 as the tang is withdrawn. The blade then simply falls into the sharps container 11 when the scalpel is withdrawn [FIG. 7].

It is to be noted that the scalpel is inserted into, and withdrawn from, the scalpel blade remover 10 in a substantially straight line path, thereby providing ease of operation.

When the scalpel is removed from the scalpel blade remover, the spring 37 pushes the slider 30 back against the inside of the front face 14 of the cover 12 to again close the opening 15. This not only serves to retain the removed blades safely and protect the blade removing mechanism from external interference, but also resets the scalpel blade remover for the next blade removal operation.

A second embodiment of the scalpel blade remover is shown in FIGS. 8-11 and its operation will be described with reference to those drawings.

The scalpel blade remover of FIGS. 8-11 has a similar housing to that of the first embodiment of FIGS. 1-7, and similar numerals are therefore used for the housing components.

The blade removing mechanism of the scalpel blade remover of FIGS. 8-11 is also similar to the blade removing mechanism of the first embodiment of FIGS. 1-7, but is fixed rather than pivoted or tilting.

As shown in FIGS. 8-11, a blade removing mechanism 40 comprises a generally planar member 41 which is similar to planar member 21 of the first embodiment. The planar member 41 has a flat upper surface which acts as a runway or platform. The planar member is fixedly mounted relative to the housing, and is mounted at an oblique angle to the direction of insertion of the tang of the scalpel.

A longitudinal slot is provided in planar member 41, in a similar manner to planar member 21. The longitudinal slot divides the planar member 41 into two spaced portions 45, 46. Two longitudinally spaced stop members 47, 48 are integrally formed on the bottom of portion 46. These stop members 47, 48 are formed by transverse ridges on the underside of portion 46, having a sawtooth configuration. The planar member 41 also has a tubular portion 41A which defines a substantially straight tunnel portion 42.

The blade removing mechanism 40 also comprises a slider block 50 which is similar to slider block 30 of the first embodiment and need not be described again. However, unlike the angled cam rod 36 of the first embodiment, the slider block 50 has a straight rod 56 extending inwardly therefrom.

When the blade removing mechanism is assembled, the planar member 41 is fixed in the housing 10, so that its upper or runway surface is at a slight downward angle relative to the landing pad 13. The rod 56 extends through the tubular portion 41A and into the aperture 18 in the internal flange 16 of the cover 12. A coil spring 57 is provided around the rod 36, between the flange 16 and the slider 50, to bias the front face of the slider against the inside of the end face 14 of the cover 12, thereby substantially closing the opening 15 in the end face 14 of the cover 12.

The operation of the blade removable mechanism 40 will now be described, with reference to FIGS. 8 to 11.

Figure 8:
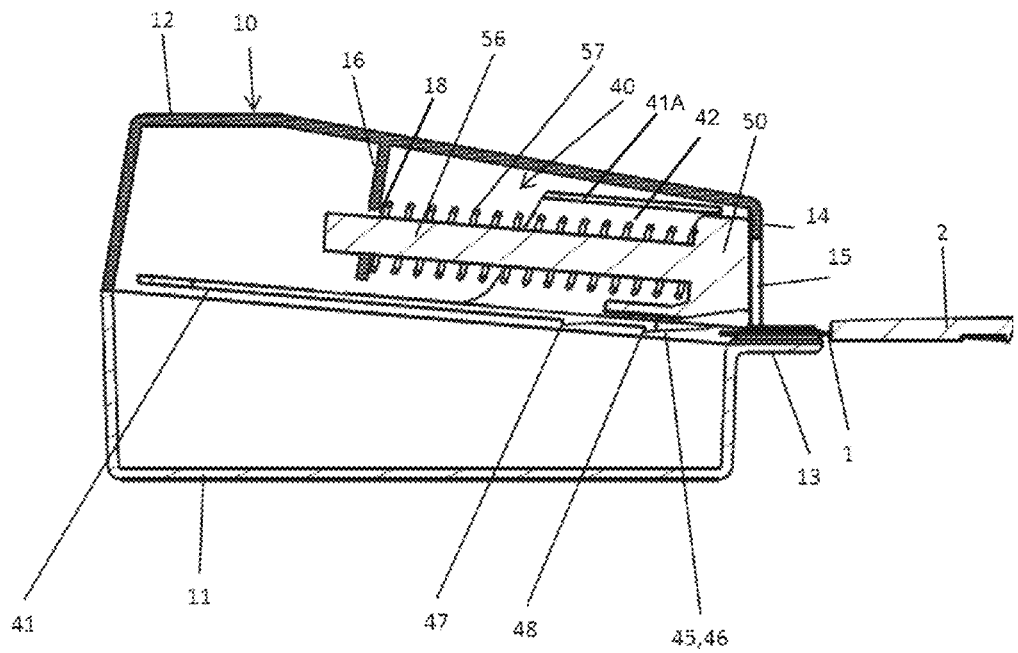
FIGS. 8 to 11 are sectional views of a scalpel blade remover according to a second embodiment of the invention, illustrating progressive steps in the blade removal process.
Figure 9:
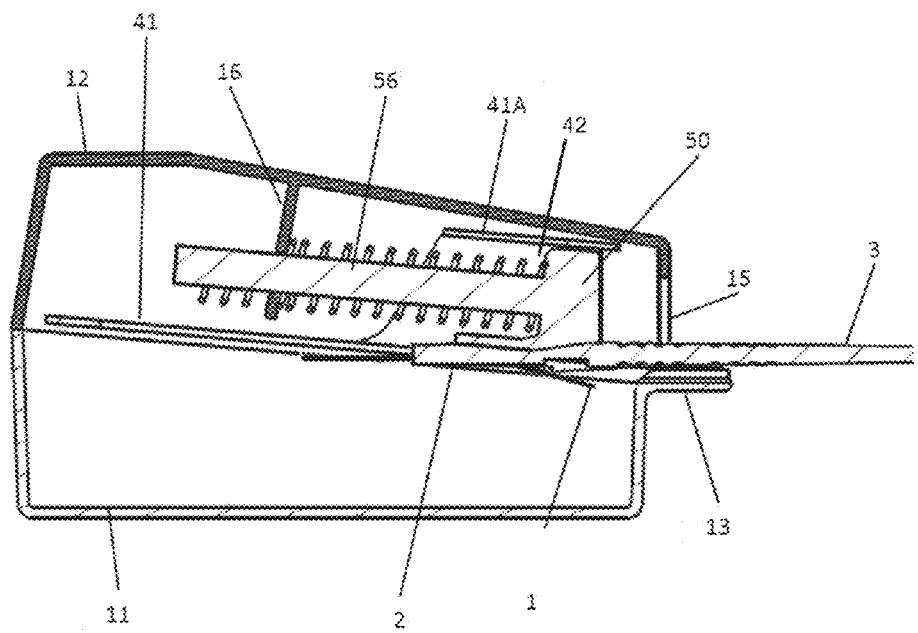

As with the first embodiment, a scalpel having a blade 1 to be removed is inserted into the scalpel blade remover 10 by first resting the tang 12 in a shallow slot on the landing pad 12, and sliding the blade 1 between the slider 50 and the landing pad 13 [FIG. 8]. The block 30 can rise up slightly to accommodate thicker blades.

The scalpel is pushed forward so that the upper part of the tang enters an opening in the slider block 50. The width of the tang 2 increases at its base, and hence when the tang is inserted far enough that the width of the tang 2 is as wide as the opening, the tang will engage the slider 50, and push the slider 50 into the cover 12. The distal or free end of the blade 1 passes under the spaced portions 45, 46.

As the slider 50 is pushed back into the tubular portion 41A by the tang 2 against the bias of the spring 57, the slider 50 slides along the runway-like portion of the planar member 41, and the bottom portion of the tang 2 travels along the longitudinal slot 24 in the planar member 41 in a similar manner to the first embodiment. However, due to the angled intersection of the planar member 41 with the tang of the scalpel, the spaced portions 45,46 of the planar member 41 are urged against the rear end or heel of blade on opposite sides of the tang in a wedge action, and separate it from the tang [FIG. 9]. The resilient nature of the blade 1 keeps it pressed against the underside of the portions 45, 46.

Figure 10:
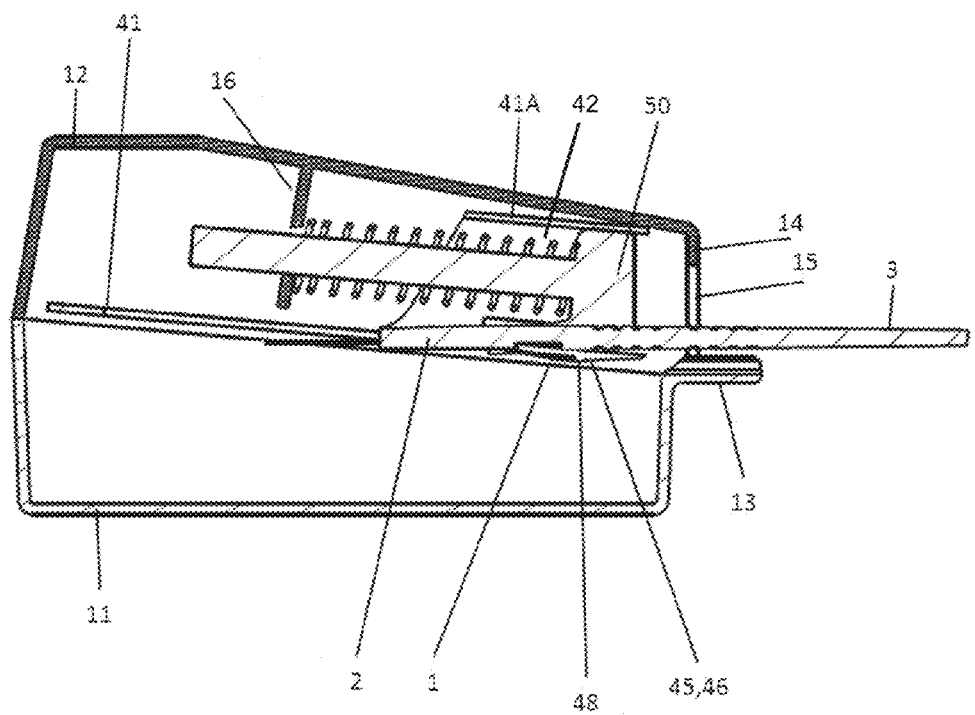
Figure 11:
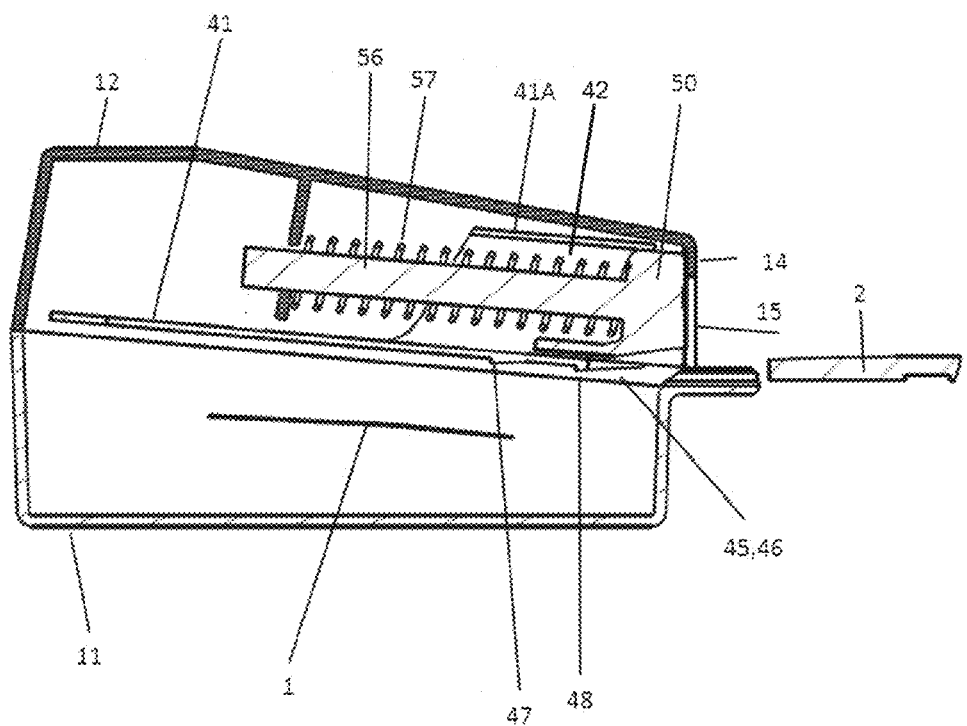

As the scalpel handle is pushed further into the opening 15, the proximal or heel end of the blade 1 will pass over the saw tooth ridge which forms the stop member 48 and snap back against the underside of the portion 46, generating an audible 'click' which indicates to the user that the scalpel has been inserted far enough and may now be withdrawn [FIG. 10]. Smaller blades may be inserted even further to engage against the distal stop member 47.

The scalpel 3 is then withdrawn. As the stop member 48 (or 47) prevents the blade 1 from being withdrawn, it is stripped from the tang 2 as the tang is withdrawn. The blade then simply falls into the sharps container 11 when the scalpel is withdrawn [FIG. 11].

As with the first embodiment, it is to be noted that the scalpel is inserted into, and withdrawn from, the scalpel blade remover 10 in a substantially straight line path, thereby providing ease of operation.

When the scalpel is withdrawn, the spring 57 pushes the slider 50 back against the inside of the front face 14 of the cover 12 to again close the opening 15.

The embodiments of the scalpel blade remover described above have several advantages over the prior art, including, without limitation, The opening 15 in the front face is large and can accommodate scalpels with large handles;

The slot 24 can expand to accommodate scalpels with large tangs;

The slider 31 can lift to accommodate thick scalpel blades;

The slit between the slider 31 and landing pad 13 is wide enough to accommodate wide scalpel blades;

The scalpel blade remover can operate with short blades or even if part of the blade has been broken off.

The cam action of the cam rod in the first embodiment creates a positive tilting force on the tilting mechanism;

The slider is constrained to move within the tunnel portion or along the planar member in a controlled manner;

The spring 37 ensures that the slider is returned to its starting position after each operation;

A user need only insert and withdraw the scalpel in a straight line to enable the blade to be removed automatically; and The dual stops 27, 28 increase the likelihood that the blade will be stripped from the tang.

The foregoing embodiments are illustrative only of the principles of the invention, and various modifications and changes will readily occur to those skilled in the art. For example, the illustrated container and cover are shown by way of example only, and the blade removing mechanism may be fitted in any other suitable housing.

Moreover, although the longitudinal axis of the tunnel 22/tubular portion 21A of the first embodiment is shown in the drawings to be parallel to the direction of insertion/withdrawal of the scalpel, it may be at a slight upward angle of attack to facilitate the tip of the scalpel passing under the tunnel 22/tubular portion 21A when it is inserted in the scalpel blade remover.

The profiled rod 36 of the first embodiment may be replaced by any other suitable cam mechanism, linkage, or other arrangement which causes the planar member 21/tubular portion 21A to tilt when the slider is pushed back by the tang.

The tubular portion 21A need not be strictly tubular but may be of any other suitable configuration to receive and engage with the slider when it is pushed back by the tang.

In yet another embodiment, the tubular portion 21A is replaced by other suitable means are provided to maintain the slider member in a close sliding relationship with the planar member. For example, the slider member may be constrained to move along rail formations along the planar member, or may engage the outer longitudinal edges of the planar member.

The scalpel blade remover may optionally include a blade counter and limiter. In one form, the blade counter comprises a ratchet counter wheel which operatively cooperates with the cam rod 36. Each time the cam rod 36 is displaced to a predetermined extent (indicating that it has been pushed in far enough by the tang of a scalpel so that the blade on the tang is engaged by the stop members and prevented from being retracted from the blade remover), its distal end will cause the counter wheel to progressively rotate by one notch and increase the count by one. The current count may be displayed by indicia on the ratchet wheel visible through a viewing window. Optionally, when the count reaches a preset maximum limit, the counter wheel does not rotate any further and presents a barrier to the inward movement of the cam rod 36, thereby preventing further use of the blade remover. This ensures that the sharps container 11 is not overfilled.

Any of the features described herein can be combined in any combination with any one or more of the other features described herein within the scope of the invention.

The term "comprise" and variants of that term such as "comprises" or "comprising" are used herein to denote the inclusion of a stated integer or integers but not to exclude any other integer or any other integers, unless in the context or usage an exclusive interpretation of the term is required.

Reference to prior art disclosures in this specification is not an admission that such disclosures constitute common general knowledge in any particular country.

INDUSTRIAL APPLICATION

The invention provides an improved method and apparatus for use in removing a blade from a scalpel, as well as a combination of such apparatus with a needle counter, which can be used in a safe manner in surgeries, laboratories and similar applications.

The invention claimed is:

1. A scalpel blade remover for removing a blade from a tang of a scalpel, the blade having a front end and a rear end, the scalpel blade remover comprising
a housing,
a generally planar member mounted in the housing, the planar member having a longitudinal slot therein between spaced portions of the planar member,
a slider member operatively associated with the planar member and adapted to slide along the planar member, the slider member having an opening for receiving at least a portion of the tang therein, the slider member being movable along the planar member when pressed by the tang of a user-held scalpel being inserted into the opening and moved along the slot in the planar member, wherein movement of the slider member along the planar member causes the spaced portions of the planar member to separate the rear end of the blade from the tang, and
at least one stop formation mechanism on the planar member which, in use, engages the rear end of the blade after it has been separated from the tang and prevents the blade being withdrawn along the planar member, such that upon withdrawal of the scalpel, the blade is stripped from the tang thereof.

2. A scalpel blade remover as claimed in claim 1, wherein the planar member has a tubular portion connected thereto, and the slider member is constrained to move within the tubular portion.

3. A scalpel blade remover as claimed in claim 2, wherein the planar member is pivotally mounted and the scalpel blade remover includes a tilting mechanism actuated by movement of the slider member along the planar member to cause the planar member to pivot or tilt, and such pivoting or tilting action causes the spaced portions of the planar member to separate the rear end of the blade from the tang.

4. A scalpel blade remover as claimed in claim 3, wherein the tubular portion has pivot pins on opposite sides thereof located in corresponding recesses in the housing, whereby the planar member is pivotally mounted to the housing.

5. A scalpel blade remover as claimed in claim 3, wherein the tilting mechanism is a cam operated mechanism comprising a cam rod extending from the slider member and having a predetermined curved or angled profile.

6. A scalpel blade remover as claimed in claim 5, further comprising a counter mechanism actuated by movement of the cam rod.

7. A scalpel blade remover as claimed in claim 6, wherein the counter mechanism is configured to disable operation of the scalpel blade remover when the counter mechanism reaches a predetermined count.

8. A scalpel blade remover as claimed in 1, wherein the planar member is fixedly mounted relative to the housing.

9. A scalpel blade remover as claimed in claim 8, wherein the planar member is mounted at an oblique angle to a direction in which the scalpel is inserted into the opening slider.

10. A scalpel blade remover as claimed in claim 1, wherein the slider member is resiliently biased to a rest position by biasing means.

11. A scalpel blade remover as claimed in claim 10, wherein the housing has a front side with an opening, and the slider member is resiliently biased to a rest position against the opening.

12. A scalpel blade remover as claimed in claim 1, wherein the planar member is made of resiliently flexible material and the longitudinal slot therein is expandable to accommodate tangs of different sizes.

13. A scalpel blade remover as claimed in claim 1, wherein the housing is generally of closed configuration and includes a container portion for collecting the blade when it is stripped from the tang.

14. A scalpel blade remover as claimed in claim 1 wherein the housing has a front side, further comprising a ledge at the front side of the housing upon which the tang may rest before insertion into the opening of the slider member.

15. A scalpel blade remover as claimed in claim 14, further comprising a narrow slit between the slider member and the ledge for accommodating the blade mounted on the tang.

16. A method of removing a scalpel blade from a tang of a scalpel, wherein the blade has a front end and a rear end, the method comprising the steps of
providing a generally planar member having a longitudinal slot therein between spaced portions of the planar member, and a slider member adapted to slide along the planar member;
inserting the tang into an opening in the slider member and into the slot, with the blade being located below the slider member;
pushing the tang against the slider member to cause the slider member slide along the planar member, with the tang moving within the longitudinal slot, until the planar member engages the rear end of the blade and prevents the blade being withdrawn along the planar member; and
withdrawing the tang so that the blade is stripped from the tang.

17. A scalpel blade remover for removing a blade from a tang of a scalpel, the blade having a front end and a rear end, the scalpel blade remover comprising
a generally planar member having a longitudinal slot therein between spaced portions of the planar member,
a slider member adapted to slide along the planar member, the slider member having an opening adjacent its bottom for receiving at least a portion of the tang therein, with the blade on the tang being located below the slider member, the slider member being movable along the planar member by being pushed by the tang moving within the longitudinal slot,
wherein movement of the slider member along the planar member causes the spaced portions of the planar member to separate the rear end of the blade from the tang and prevent the blade being withdrawn along the planar member, such that upon withdrawal of the scalpel, the blade is stripped from the tang thereof.

18. A scalpel blade remover as claimed in claim 17, wherein the planar member is made of resiliently flexible material and the longitudinal slot therein is expandable to accommodate tangs of different sizes.

19. A scalpel blade remover as claimed in claim 17, wherein the planar member and slider member are located within a housing, and the planar member is pivotally mounted to the housing.

20. A scalpel blade remover as claimed in claim 17, wherein the planar member and slider member are located within a housing, and the planar member is fixedly mounted relative to the housing.

* * * * *